United States Patent [19]
Bowman

[11] Patent Number: 5,226,815
[45] Date of Patent: Jul. 13, 1993

[54] DENTAL COVERING

[76] Inventor: Karolen C. Bowman, P.O. Box 2084, North Wilkesboro, N.C. 28659

[21] Appl. No.: 987,371

[22] Filed: Dec. 7, 1992

[51] Int. Cl.⁵ .......................... A61C 5/14; A61B 19/08
[52] U.S. Cl. ...................................... 433/137; 128/853
[58] Field of Search ................ 433/136, 137; 128/849, 128/850, 851, 852, 853, 854, 855, 858

[56] References Cited

U.S. PATENT DOCUMENTS

| | | | |
|---|---|---|---|
| 3,060,932 | 10/1962 | Pereny et al. | 128/849 |
| 3,455,302 | 7/1969 | Liloia et al. | 128/132 |
| 3,503,391 | 3/1970 | Melges | 128/852 |
| 3,561,439 | 2/1971 | Bayer | 128/853 |
| 3,565,067 | 2/1971 | Bayer | 128/853 |
| 3,668,050 | 6/1972 | Donnelly | 161/39 |
| 3,902,484 | 9/1975 | Winters | 128/132 |
| 4,067,327 | 1/1978 | Shannon, Sr. | 128/132 |
| 4,344,758 | 8/1982 | Wielhouwer et al. | 433/137 |
| 4,384,573 | 5/1983 | Elliott | 128/853 |
| 4,626,211 | 12/1986 | Coston | 433/137 |
| 4,771,480 | 9/1988 | Stimson et al. | 2/88 |
| 4,969,473 | 11/1990 | Bothwell | 128/858 |
| 5,127,423 | 7/1992 | Graeger | 128/854 X |

Primary Examiner—John J. Wilson
Assistant Examiner—Nicholas D. Lucchesi
Attorney, Agent, or Firm—Bell, Seltzer, Park & Gibson

[57] ABSTRACT

A dental covering of such a size as to drape over a patient's upper torso and head to protect the patient from airborne moisture and contaminants caused by dental work on the patient, the dental covering being substantially rectangular in overall shape and at least several feet in length and width so as to overlie a patient's upper torso and head during dental work. The dental covering has upper and lower fabric sections adapted to respectively overlie the head and torso of the patient and an intermediate fabric section bridging and joining the upper and lower fabric sections and adapted to extend across a patient's eyes. Each of the fabric sections is substantially parallel to each other and has a common lengthwise extent adapted to extend transversely across the patient. The intermediate fabric section is formed of transparent material for psychological enhancement of patient comfort and the upper and lower fabric sections are formed of an absorbent material for absorbing and collecting the moisture and contaminants during dental work. The lower fabric section has an opening therein for access to the patient's mouth. The opening in the lower fabric section is positioned closely adjacent the intermediate transparent fabric section.

15 Claims, 2 Drawing Sheets

DENTAL COVERING

FIELD OF THE INVENTION

This invention relates to face protection devices and more particularly to a dental covering for protecting a patient from airborne moisture and contaminants caused by dental work on the patient.

BACKGROUND OF THE INVENTION

Currently, when a dental patient has dental work performed, various tools are used for scaling calculus from the teeth of the patient and for cooling or rinsing the patient's mouth. These tools include vibratory instruments for spraying, polishing, or cleaning the teeth and surrounding internal mouth area, i.e., gums. As a result of the use of these various tools, moisture and contaminants from the mouth or tools are often sprayed onto the patient's face, neck, and upper torso causing discomfort and unsanitary conditions.

Dental shields have been developed to cover the patient's face and neck to attempt to prevent this discomfort and these unsanitary conditions. Examples of these dental shield may be seen in U.S. Pat. No. 4,969,473 by Bothwell entitled "Dental Patient Face And Neck Shield"; and U.S. Pat. No. 4,344,758 by Wielhouwer et al. entitled "Dental Face Shield." These conventional dental shields, however, fail to adequately cover the head and upper torso of the patient, are bulky and awkward for easy use, or constrain the patient so as to cause psychological discomfort.

Thus, there is a need for a dental shield or dental covering which is easy to use, adequately covers the head and upper torso of the patient, and provides psychological comfort to the patient during use.

SUMMARY OF THE INVENTION

Therefore, the present invention provides a dental covering of such a size as to drape over a patient's upper torso and head to protect the patient from airborne moisture and contaminants caused by dental work on the patient. The dental covering is easily placed on the patient and does not enclose or constrain the patient so as to cause psychological discomfort.

More particularly, the dental covering is substantially rectangular in overall shape and at least several feet in length and width so as to overlie the patient's upper torso and head during dental work. The dental covering has upper and lower fabric sections adapted to respectively overlie the head and torso of the patient and an intermediate fabric section bridging and joining said upper and lower fabric sections and adapted to extend across a patient's eyes. Each of the fabric sections is substantially parallel to each other and has a common lengthwise extent adapted to extend transversely across the patient. The intermediate fabric section is formed of transparent material for psychological enhancement of patient comfort and the upper and lower fabric sections are formed of an absorbent material for absorbing and collecting the moisture and contaminants during dental work. The lower fabric section has an opening therein for access to the patient's mouth. The mouth opening in the lower fabric section is generally positioned closely adjacent the intermediate transparent fabric section.

BRIEF DESCRIPTION OF THE DRAWINGS

Some of the objects and advantages of the present invention having been stated, others will become apparent as the description proceeds when taken in conjunction with the accompanying drawings, in which.

DESCRIPTION OF A PREFERRED EMBODIMENT

The present invention now will be described more fully hereinafter with reference to the accompanying drawings in which a preferred embodiment of the invention is shown. Like numbers refer to like elements throughout.

Figure 1:
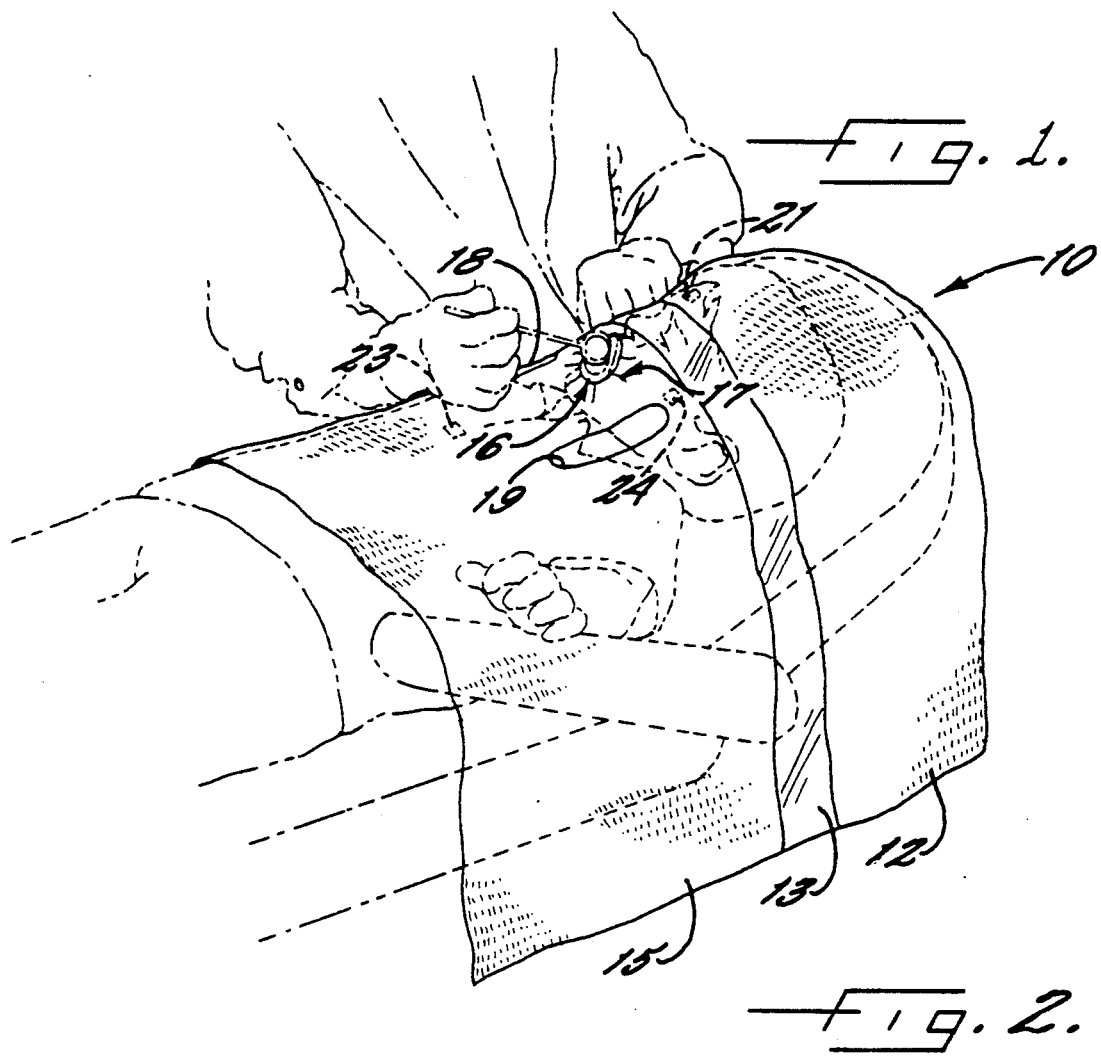
FIG. 1 is an environmental view of the dental covering according to the present invention in use with a child patient in a dental chair and a dental worker illustrated in phantom view.

Referring now to the drawings, FIG. 1 is an environmental view of the dental covering according to the present invention broadly designated at 10. FIG. 1 further shows a child patient in a dental chair and a dental worker in phantom view. The dental covering 10 is of such a size as to drape over the patient's upper torso and head to protect the patient from airborne moisture and contaminants caused by dental work on the patient.

Figure 2:
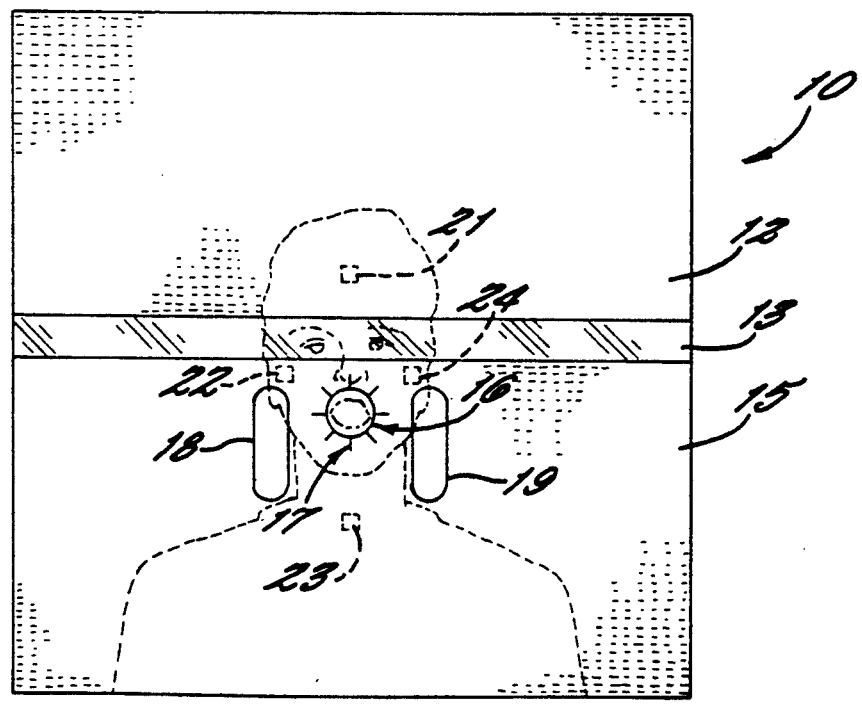
FIG. 2 is a top plan view of the dental covering according to the present invention with an adult patient illustrated in phantom view.

FIG. 2 shows a top plan view of the dental covering 10 according to the present invention with an adult patient illustrated in phantom view. The dental covering 10 is substantially rectangular in overall shape and generally at least several feet in length and width so as to overlie the patient's upper torso and head during dental work. The overall length of the dental covering 10 is preferably 36 inches and the overall width of the dental covering 10 is preferably 45 inches. The dental covering 10 has upper 12 and lower 15 fabric sections adapted to respectively overlie the head and torso of the patient and an intermediate fabric section 13 bridging and joining the upper 12 and lower 15 fabric sections and adapted to extend across the patient's eyes. Each of the fabric sections 12, 13, 15 is substantially parallel to each other and has a common lengthwise extent adapted to extend transversely across the patient. The intermediate fabric section 13 is formed of transparent material for psychological enhancement of patient comfort and the upper 12 and lower 15 fabric sections are formed of an absorbent material for absorbing and collecting the moisture and contaminants during dental work. The upper 12 and lower 15 fabric sections are also formed of multilayer fabric as discussed more fully below with reference to FIGS. 4 and 5.

The lower fabric section 15 has an opening 16 therein for access to the patient's mouth. The mouth opening 16 is positioned closely adjacent the intermediate transparent fabric section 13. The lower fabric section 15 also has radially displaced slits, shown generally at 17, along the mouth opening 16 in the lower fabric section 15. These radially displaced slits 17 provide slack in the fabric of the lower fabric section 15 to enhance access to the mouth of the patient, decrease bunching of the fabric during use, and facilitate the accommodation of the mouth opening 16 to various size mouths. The lower fabric section 15 further has a pair of ventilation slits 18, 19 in an upper portion of the lower fabric section 15 for providing ventilation to enhance the breathing of the patient when the dental covering 10 is being used.

Also illustrated in FIG. 2 is a phantom view of securing means, shown generally by four adhesive tabs 21, 22, 23, 24, carried by the dental covering 10 for securing the dental covering 10 to the patient. The underside of the upper 12 and lower 15 fabric sections of the dental covering 10 carry the adhesive tabs 21, 22, 23, 24 for respectively and adhesively securing the upper 12 and lower 15 fabric sections of the dental covering 10 to the patient's head and upper torso. The adhesive tabs 21, 22, 23, 24 are generally rectangular in shape and have an adhesive material thereon for whereupon removal of a tape covering of the adhesive material provides a means for securing the respective upper 12 and lower 15 fabric sections to the forehead, cheeks, and upper torso of the patient.

Figure 3:
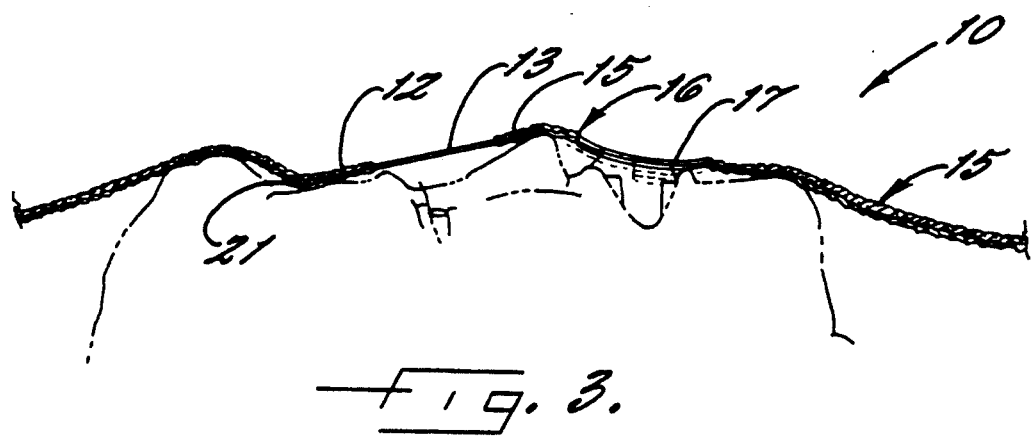
FIG. 3 is side cross sectional view of the dental covering, with parts broken away for clarity, draped across a patient's head illustrated in phantom view.

FIG. 3 illustrates a side cross-sectional view of the dental covering 10, with parts broken away for clarity, being draped across a patient's head shown in phantom view. This view further shows the interconnecting upper 12, lower 15, and intermediate 13 fabric sections of the dental covering 10 and the position of the mouth opening 16 in the lower fabric section 15 for access to the patient's mouth.

Figure 4:
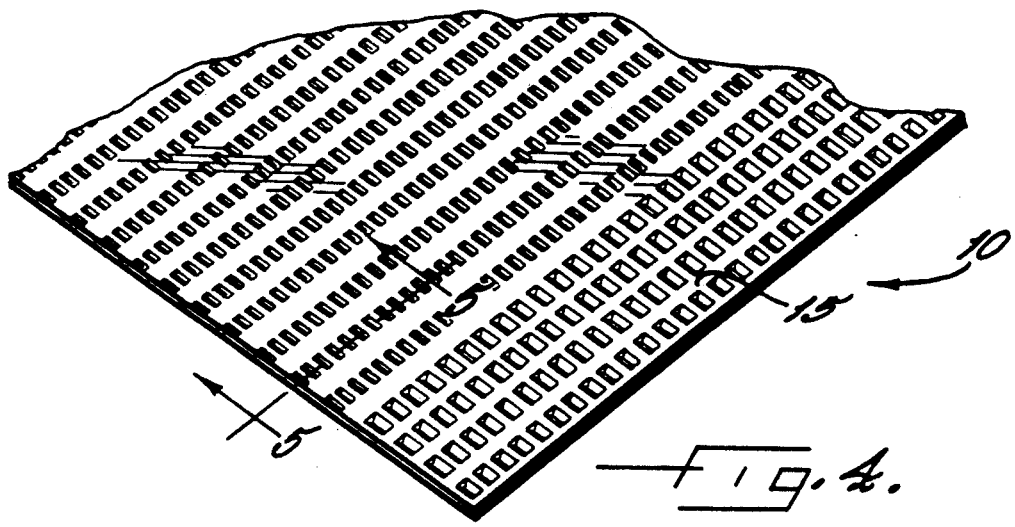
FIG. 4 is an enlarged fragmentary view of the dental covering according to the present invention.
Figure 5:
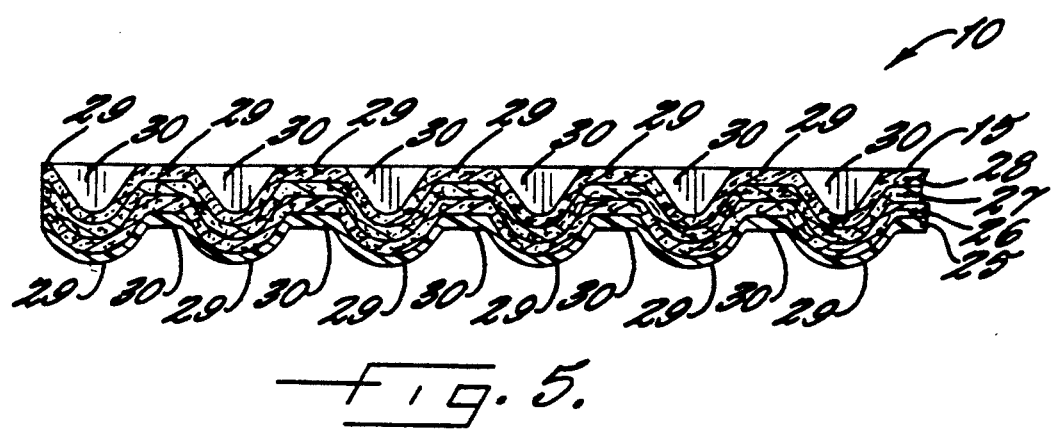
FIG. 5 is an enlarged fragmentary cross sectional view of the dental covering taken along line 5—5 of FIG. 4.

FIGS. 4 and 5 further illustrate the construction of the fabric forming the upper 12 and lower 15 fabric sections of the dental covering 10. FIG. 4 is an enlarged fragmentary view of the dental covering 10 according to the present invention and FIG. 5 is an enlarged cross-sectional view of the dental covering 10 taken along line 5—5 of FIG. 4. As shown in these views, a multilayer fabric forms the upper 12 and lower 15 fabric sections of the dental covering 10. The multilayer fabric has a layer 25 of moisture impervious material, preferably a polymeric material, for protecting the patient from the moisture and contaminants and three overlying layers 26, 27, 28 of moisture absorbing material, preferably paper material, overlying the moisture impervious material for providing absorption and collection of the moisture and contaminants on the dental covering 10. Also, as illustrated in FIGS. 4 and 5, the polymeric 25 and paper 26, 27, 28 layers are embossed to form a plurality of ridges 29 in the upper 12 and lower 15 multilayer fabric sections for enhancement of appearance and for reducing static when the dental covering 10 is being unfolded and placed on and removed from the patient. The ridges 29 are formed on both the top and underside of the multilayer fabric and are preferably spaced apart to also provide concave portions 3D between the ridges 29. The illustrated embossed multilayer fabric of this invention is well known for use in the dental field as a protective device for patients. It will be apparent to those skilled in the art that other fabric material besides the embossed multilayer fabric material may also be used.

In the drawings and specification, there has been disclosed a typical preferred embodiment of the invention and, although specific terms are employed, they are used in a generic and descriptive sense only and not for the purposes of limitation, the scope of the invention being set forth in the following claims.

That which is claimed is:

1. A dental covering of such a size as to drape over a patient's upper torso and head to protect the patient from airborne moisture and contaminants caused by dental work on the patient, said dental covering being substantially rectangular in overall shape and at least several feet in length and width so as to overlie a patient's upper torso and head during dental work, said dental covering further comprising upper and lower fabric sections adapted to respectively overlie the head and torso of the patient and an intermediate fabric section bridging and joining said upper and lower fabric sections and adapted to extend across a patient's eyes, each of said fabric sections being substantially parallel to each other and having a common lengthwise extent adapted to extend transversely across the patient, said intermediate fabric section being formed of transparent material for psychological enhancement of patient comfort, said upper and lower fabric sections being formed of an absorbent material for absorbing and collecting the moisture and contaminants during dental work, and said lower fabric section having an opening therein for access to the patient's mouth, said opening being positioned closely adjacent said intermediate transparent fabric section.

2. A dental covering according to claim 1, wherein said lower fabric section further comprises radially displaced slits along said mouth opening in said lower fabric section for facilitating accommodation to various size mouths.

3. A dental covering according to claim 1, wherein said lower fabric section further comprises ventilation slits in an upper portion thereof for providing ventilation to enhance the breathing of the patient when the dental covering is being used.

4. A dental covering according to claim 1, further comprising securing means carried by the dental covering for securing the dental covering to the patient.

5. A dental covering according to claim 1, wherein said upper and lower fabric sections are formed of multilayer fabric.

6. A dental covering according to claim 5, wherein said multilayer fabric comprises a layer of moisture impervious material on an underside for protecting the patient from the moisture and contaminants and a layer of moisture absorbing material overlying said moisture impervious material for providing absorption and collection of the moisture and contaminants on the dental covering.

7. A dental covering according to claim 6, wherein said moisture impervious layer comprises a polymeric material and wherein said moisture absorbing layer comprises paper.

8. A dental covering according to claim 7, wherein said polymeric and paper layers are embossed to form a plurality of ridges in said upper and lower multilayer fabric sections for enhancement of appearance and for reducing static when the dental covering is being unfolded and placed on and removed from the patient.

9. A dental covering of such a size as to drape over a patient's upper torso and head to protect the patient from airborne moisture and contaminants caused by dental work on the patient, said dental covering being substantially rectangular in overall shape and at least several feet in length and width so as to overlie a patient's upper torso and head during dental work, said dental covering further comprising upper and lower multilayer fabric sections adapted to respectively overlie the head and torso of the patient and an intermediate fabric section bridging and joining said upper and lower multilayer fabric sections and adapted to extend across a patient's eyes, each of said fabric sections being substantially parallel to each other and having a common lengthwise extent adapted to extend transversely across the patient, said intermediate fabric section being formed of transparent polymeric material for psychological enhancement of patient comfort, said upper and lower multilayer fabric sections being formed of a moisture impervious material and an overlying absorbent material for absorbing and collecting the moisture and contaminants during dental work and for protecting the patient from the moisture and contaminants, and said lower multilayer fabric section having an opening therein positioned closely adjacent said intermediate fabric section for access to the patient's mouth and ventilation slits in an upper portion of said lower multilayer fabric section for providing ventilation to enhance the breathing of the patient when the dental covering is being used.

10. A dental covering according to claim 9, further comprising adhesive tabs carried by an underside of said upper and lower multilayer fabric sections of the dental covering for respectively and adhesively securing said upper and lower multilayer fabric sections of the dental covering to the patient's head and upper torso.

11. A dental covering according to claim 9, wherein said lower multilayer fabric section further comprises radially displaced slits along said mouth opening in said lower multilayer fabric section.

12. A dental covering according to claim 9, wherein said multilayer fabric comprises a layer of polymeric material for protecting the patient from the moisture and contaminants and a plurality of layers of paper material overlying said polymeric material for providing absorption and collection of the moisture and contaminants on the dental covering.

13. A dental covering according to claim 12, wherein said polymeric and paper layers are embossed to form a plurality of ridges in said upper and lower fabric sections for enhancement of appearance and for reducing static when the dental covering is being unfolded and place on and removed from the patient.

14. A dental covering of such a size as to drape over a patient's upper torso and head to protect the patient from airborne moisture and contaminants caused by dental work on the patient, said dental covering being substantially rectangular in overall shape and at least several feet in length and width so as to overlie a patient's upper torso and head during dental work, said dental covering further comprising upper and lower multilayer fabric sections adapted to respectively overlie the head and torso of the patient and an intermediate fabric section bridging and joining said upper and lower multilayer fabric sections and adapted to extend across a patient's eyes, each of said fabric sections being substantially parallel to each other and having a common lengthwise extent adapted to extend transversely across the patient, said intermediate fabric section being formed of transparent polymeric material for psychological enhancement of patient comfort, said upper and lower multilayer fabric sections being formed of a layer of polymeric material for protecting the patient from the moisture and contaminants and a plurality of overlying layers of paper material for absorbing and collecting the moisture and contaminants during dental work, said polymeric and paper layers being embossed to form a plurality of ridges in said upper and lower fabric sections for enhancement of appearance and for reducing static when the dental covering is being handled, and said lower multilayer fabric section having an opening therein positioned closely adjacent said intermediate fabric section for access to the patient's mouth, radially displaced slits along said mouth opening in said lower multilayer fabric section, and ventilation slits in an upper portion of said lower multilayer fabric section for providing ventilation to enhance the breathing of the patient when the dental covering is being used.

15. A dental covering according to claim 14, further comprising adhesive tabs carried by an underside of said upper and lower multilayer fabric sections of the dental covering for respectively and adhesively securing said upper and lower multilayer fabric sections of the dental covering to the patient's head and upper torso.

* * * * *